United States Patent [19]

Rink et al.

[11] Patent Number: 5,354,843

[45] Date of Patent: Oct. 11, 1994

[54] FLANKING PEPTIDES OF CALCITONIN AND PROCESSES FOR THEIR MANUFACTURE

[75] Inventors: Hans Rink, Riehen; Klaus Müller, Ettingen, both of Switzerland

[73] Assignee: Ciba-Geigy Corporation, Ardsley, N.Y.

[21] Appl. No.: 398,120

[22] Filed: Aug. 23, 1989

[30] Foreign Application Priority Data

Aug. 26, 1988 [CH] Switzerland ............... 3174/88.0

[51] Int. Cl.$^5$ ............... C07K 7/00; C07K 1/06; A61K 37/30
[52] U.S. Cl. ............... 530/307; 530/324; 530/402
[58] Field of Search ............... 530/307, 324, 402; 514/12

[56] References Cited

PUBLICATIONS

G. Komos et al., J. Biol. Chem. 361, 14386–14391 (1986).
Burns et al., *FASEB J.* (295) #4949 (1988).
Burn et al. *Clin. Res.* 36(1) 1504 (1988).
Howard et al. Abstracts, Conference on Calcium Regulating Hormones Joint Mtg. Sep. 9–14, 1989, Montreal, Canada (1989) #571.

*Primary Examiner*—Robert J. Hill, Jr.
*Assistant Examiner*—Shelly Guest Cermak
*Attorney, Agent, or Firm*—Karen G. Kaiser; Irving M. Fishman

[57] ABSTRACT

Peptides of formula I

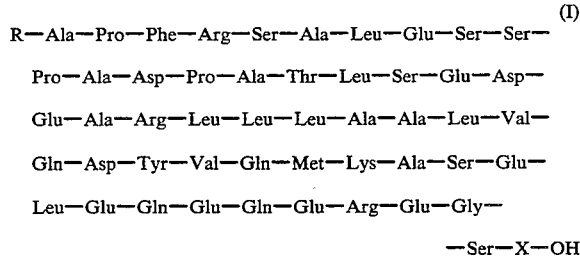

in which R is hydrogen or acetyl and X is an amino acid sequence of formula -Ser-Leu-Asp-Ser-Pro-Arg-Ser- (Ia) or of formula -Arg-Ile-Ile-Ala-Gln- (Ib), and salts of such compounds, can be used for the treatment of diseases involving bone degeneration.

6 Claims, No Drawings

FLANKING PEPTIDES OF CALCITONIN AND PROCESSES FOR THEIR MANUFACTURE

The invention relates to novel peptides, especially human procalcitonin N-terminal-flanking peptides, to salts thereof, to certain DNA sequences and microorganisms that contain such DNA sequences and that are capable of producing the peptides of the invention, as intermediates for the manufacture of these peptides, to processes for the manufacture of the peptides or DNA sequences, to pharmaceutical preparations that contain the said peptides or salts thereof, and to the use of these peptides or salts thereof as medicaments.

The invention relates especially to peptides of formula I

in which R is hydrogen or acetyl and X is an amino acid sequence of formula -Ser-Leu-Asp-Ser-Pro-Arg-Ser- (Ia) or of formula -Arg-Ile-Ile-Ala-Gln- (Ib), especially peptides of formula

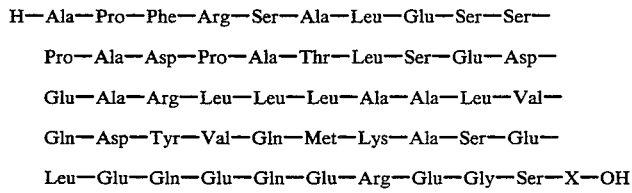

in which X is preferably an amino acid sequence of formula Ia (PCATFP: human procalcitonin amino-terminal flanking peptide), also called PAS-57 (peptide alanine serine-57), or is that of formula Ib (PCGRPATFP: human procalcitonin gene related peptide amino-terminal flanking peptide), and to salts of such peptides.

In agreement with the internationally recognised nomenclature rules, the abbreviations for amino acids in this Application, such as, for example, the above-mentioned abbreviations, indicate the free acid and, unless stated otherwise, the L-configuration thereof. The α-amino group is in each case to be considered to be at the left-hand side of the abbreviation, the carboxy group at the right-hand side. The absence of an H atom in the α-amino group is marked by a hyphen positioned to the left of the abbreviation for the amino acid, and the absence of an HO group in the carboxy group by a hyphen positioned to the right. Substituents in the side chain of free amino acids or radicals thereof are placed in brackets directly after the amino acid symbol.

After the priority date of the present application it was found that the peptides of the invention occur as such in the human organism. The invention therefore relates especially to the above-mentioned peptides and salts thereof in a higher concentration than occurs naturally or in extracts that may be known. In particular, the invention relates to the above-mentioned peptides in isolated or enriched form, in pure or substantially pure form, in a substantially different surrounding, that is to say with other admixtures, for example admixed pharmaceutical carriers, than those which occur naturally, in a form suitable for pharmaceutical use, in characterised form and/or in a form outside of a living or dead organism, of an organ, of a cell, of a tissue or of a body fluid. The invention relates especially to synthetically or genetically produced peptides of formula I and their salts.

In the above connection, the term "isolated" means separated from other substances, especially from other chemical compounds, with which the compounds of the invention may occur naturally. The term "purified" means subjected to chemical and/or physical purification methods. The expression "substantially pure" means a purity of more than 50%.

The invention relates also to the salts, especially the pharmaceutically acceptable non-toxic salts, of the peptides according to the invention. The above-mentioned peptides can form acid addition salts, for example with inorganic acids, especially mineral acids, for example hydrochloric acid, sulfuric acid or phosphoric acid, or salts with organic carboxylic, sulfonic or sulfo acids, for example acetic acid, propionic acid, glycolic acid, succinic acid, maleic acid, hydroxymaleic acid, methylmaleic acid, fumaric acid, malic acid, tartaric acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, also amino acids, as well as methanesulfonic acid, ethanesulfonic acid, 2-hydroxyethanesulfonic acid, ethane-1,2-disulfonic acid, benzenesulfonic acid, 4-methylbenzenesulfonic acid or naphthalene-2-sulfonic acid, or with other acidic organic compounds, such as ascorbic acid.

The above-mentioned peptides can also form metal or ammonium salts, such as alkali metal and alkaline earth metal salts, for example sodium, potassium, magnesium or calcium salts, as well as ammonium salts with ammonia or suitable organic amines, there being suitable for the salt formation especially aliphatic, cycloaliphatic, cycloaliphatic-aliphatic or araliphatic primary, secondary or tertiary mono-, di- or poly-amines, and also heterocyclic bases, such as lower alkylamines, for example triethylamine, hydroxy-lower alkylamines, for example 2-hydroxyethylamine, bis-(2-hydroxyethyl)-amine, 2-hydroxyethyl-diethylamine or tri-(2-hydroxyethyl)-amine, basic aliphatic esters of carboxylic acids, for example 4-aminobenzoic acid 2-diethylaminoethyl ester, lower alkyleneamines, for example 1-ethylpiperidine, cycloalkylamines, for example dicyclohexylamine, or benzylamines, for example N,N'-dibenzylethylenediamine, and also bases of the pyridine type, for example pyridine, collidine or quinoline.

The above-mentioned peptides can, in addition, form internal salts.

For isolation or purification it is also possible to use salts that are not pharmaceutically suitable. Only the pharmaceutically acceptable non-toxic salts, however, are used therapeutically, and these are therefore preferred.

The compounds according to the invention can be manufactured in a manner known per se, for example as follows a) an amide bond present in a compound having the amino acid sequence of formula I is formed by reaction of a fragment of such a compound that has a reactive free carboxy group, or of a reactive carboxylic acid derivative thereof, with the complementary fragment of such a compound that has a free amino group, or with a reactive derivative thereof, wherein free functional groups in the mentioned fragments, with the exception of the two groups participating in the reaction, are, if necessary, in protected form, and protecting groups which may be present are removed, or b) host cells transformed with an expression vector containing a DNA sequence that codes for the amino acid sequence of formula I and that is regulated by an expression control sequence are propagated, and a compound having the amino acid sequence of formula I is, if necessary, freed from the host cells and isolated, and, if necessary, in a compound obtainable in accordance with the invention having a sulfoxide grouping, this grouping is converted into a thio group and, if desired, a salt obtainable in accordance with the process is converted into the free compound and/or a free compound obtainable in accordance with the process is converted into a salt.

Process a

According to this process, as the last stage of the reaction in the synthesis of the end product an amide bond is linked to any position of the amino acid sequence of formula I. The mentioned fragment that contains a free carboxy group may be either a single amino acid or a di-, oligo- or poly-peptide. The fragment that contains a free amino group is also a single amino acid, a di-, oligo- or poly-peptide.

Preferably, the reaction is carried out by reacting a reactive carboxylic acid derivative of the one fragment with the complementary fragment that contains a free amino group, it being possible for the derivatisation of the carboxy group of the carboxylic acid fragment to be effected in situ.

Reactive carboxylic acid derivatives are especially reactive activated esters or reactive anhydrides, and also reactive cyclic amides; as mentioned, reactive carboxylic acid derivatives can be formed in situ.

Activated esters of acids are especially esters that are unsaturated at the linking carbon atom of the esterifying radical, for example of the vinyl ester type, such as true vinyl esters (which can be obtained, for example, by the transesterification of a corresponding ester with vinyl acetate; activated vinyl ester method), carbamoylvinyl esters (which can be obtained, for example, by treating the corresponding acid with an isoxazolium reagent; 1,2-oxazolium or Woodward method), or 1-lower alkoxyvinyl esters (which can be obtained, for example, by treating the corresponding acid with a lower alkoxyacetylene; ethoxyacetylene method), or esters of the amidino type, such as N,N'-disubstituted amidino esters (which can be obtained, for example, by treating the corresponding acid with a suitable N,N'-disubstituted carbodiimide, for example N,N'-diisopropyl- or N,N'-dicyclohexyl-carbodiimide; carbodiimide method), or N,N-disubstituted amidino esters (which can be obtained, for example, by treating the corresponding acid with an N,N-disubstituted cyanamide; cyanamide method). Activated esters are also, for example, suitable aryl esters, especially phenyl esters suitably substituted by electron-attracting substituents (which esters can be obtained, for example, by treating the corresponding acid with a suitably substituted phenol, for example 4-nitrophenol, 4-methylsulfonylphenol, 2,4,5-trichlorophenol, 2,3,4,5,6-pentachlorophenol or 4-phenyldiazophenol, in the presence of a condensing agent, such as N,N'-dicyclohexylcarbodiimide; activated aryl esters method) cyanomethyl esters (which can be obtained, for example, by treating the corresponding acid with chloroacetonitrile in the presence of a base; cyanomethyl esters method), suitable thioesters, especially phenylthio esters that are unsubstituted or substituted, for example, by nitro (which can be obtained, for example, by treating the corresponding acid with a thiophenol that is unsubstituted or substituted, for example, by nitro, inter alia with the aid of the anhydride or carbodiimide method; activated thiol esters method), or amino or amido esters (which can be obtained, for example, by treating the corresponding acid with an N-hydroxyamino or N-hydroxyamido compound, for example N-hydroxysuccinimide, N-hydroxypiperidine, N-hydroxyphthalimide or 1-hydroxy-1H-benzotriazole, for example according to the anhydride or carbodiimide method; activated N-hydroxy esters method).

Reactive acid anhydrides may be symmetrical or preferably mixed anhydrides of these acids, for example anhydrides with inorganic acids, such as acid halides, especially acid chlorides (which can be obtained, for example, by treating the corresponding acid with a suitable halogenating agent, such as thionyl chloride, phosphorus pentachloride or oxalyl chloride; acid chloride method); azides (which can be obtained, for example, from an acid ester by way of the corresponding hydrazide and treatment thereof with nitrous acid; azide method), anhydrides with carbonic acid semi-derivatives, such as with corresponding esters, for example carbonic acid lower alkyl semi-esters (which can be obtained, for example, by treating the corresponding acid with haloformic, such as chloroformic, acid lower alkyl esters or with a 1-lower alkoxycarbonyl-2-lower alkoxy-1,2-dihydroquinoline, for example 1-lower alkoxycarbonyl-2-ethoxy-1,2-dihydroquinoline; mixed O-alkylcarbonic acid anhydrides method), or anhydrides with dihalogenated, especially dichlorinated, phosphoric acid (which can be obtained, for example, by treating the corresponding acid with phosphorus oxychloride; phosphorus oxychloride method), or anhydrides with organic acids, such as mixed anhydrides with organic carboxylic acids (which can be obtained, for example, by treating the corresponding acid with an unsubstituted or substituted lower alkanecarboxylic or phenyl-lower alkanecarboxylic acid halide, for example phenylacetic acid, pivalic acid or trifluoroacetic acid chloride; mixed carboxylic acid anhydrides method) or with organic sulfonic acids (which can be obtained, for example, by treating a salt, such as an alkali metal salt, of the corresponding acid with a suitable organic sulfonic acid halide, such as a lower alkanesulfonic or arylsulfonic acid chloride, for example methane- or p-toluene-sulfonic acid chloride; mixed sulfonic acid anhydrides method), as well as symmetrical anhydrides (which can be obtained, for example, by condensation of the corresponding acid in the presence of a carbodiimide or of 1-diethylaminopropyne; symmetrical anhydrides method).

Suitable cyclic amides are especially amides with five-membered diazacycles of aromatic character, such as amides with imidazoles, for example imidazole (which can be obtained, for example, by treating the corresponding acid with N,N'-carbonyldiimidazole; imidazolide method) or pyrazoles, for example 3,5-dimethylpyrazole (which can be obtained, for example, by way of the acid hydrazide by treatment with acetylacetone; pyrazolide method).

As mentioned, the carboxylic acid derivatives can also be formed in situ. For example, N,N'-disubstituted amidino esters can be formed in situ by reacting a mixture of the complementary fragment having the free amino group and the peptide fragment having a free carboxy group in the presence of a suitable N,N-disubstituted carbodiimide, for example N,N-diisopropyl- or N,N'-dicyclohexyl-carbodiimide. Further, amino or amido esters of acids can be formed in the presence of the amine to be acylated by reacting a mixture of the corresponding acid and amino starting materials in the presence of an N,N'-disubstituted carbodiimide, for example N,N'-dicyclohexyl- or N,N'-diisopropyl-carbodiimide, and in the presence of an N-hydroxyamine or N-hydroxyamide, for example N-hydroxysuccinimide, optionally in the presence of a suitable base, for example 4-dimethylaminopyridine.

Alternatively, process variant a) can also be carried out by reacting a fragment having a free carboxy group with the complementary fragment in which the amino group is present in reactive form; the amino group can be activated, for example, by reaction with a phosphite, for example diethyl chlorophosphite, 1,1-phenylene chlorophosphite, ethyl dichlorophosphite, ethylene chlorophosphite or tetraethyl pyrophosphite, or with a suitable silylation agent, such as an organic halosilane, for example trimethylchlorosilane. The amino group can also be activated by bonding to halocarbonyl, for example chlorocarbonyl, or can be activated in the form of an isocyanate group.

Functional groups in the mentioned fragments which, if they are not to participate in the reaction, are advantageously in protected form, are especially carboxy, amino and hydroxy groups, and also carbamoyl and guanidino groups.

Protecting groups and the manner in which they are introduced and removed are described, for example, in "Protective Groups in Organic Chemistry", Plenum Press, London, N.Y. 1973, and in "Methoden der organischen Chemie", Houben-Weyl, 4th Edition, Vol. 15/1, Georg-Thieme-Verlag, Stuttgart 1974, and in Theodora W. Greene, "Protective Groups in Organic Synthesis", John Wiley & Sons, New York 1981. It is characteristic of protecting groups that they can be readily removed, that is to say without undesired secondary reactions taking place, for example by solvolysis, reduction or photolysis.

Hydroxy-protecting groups are, for example, acyl radicals, such as unsubstituted or substituted, for example halo-substituted, lower alkanoyl, such as 2,2-dichloroacetyl, or acyl radicals of carbonic acid semiesters, especially tert.-butoxycarbonyl, unsubstituted or substituted benzyloxycarbonyl, for example 4-nitrobenzyloxycarbonyl, or diphenylmethoxycarbonyl, or 2-halo-lower alkoxycarbonyl, such as 2,2,2-trichloroethoxycarbonyl, or formyl. Other hydroxy-protecting groups are, for example, suitable etherifying groups, such as trityl, tert.-lower alkyl, for example tert.-butyl, 2-oxa- or 2-thia-aliphatic or -cycloaliphatic hydrocarbon radicals, especially 1-lower alkoxy-lower alkyl or 1-lower alkylthio-lower alkyl, for example methoxymethyl, 1-methoxyethyl, 1-ethoxyethyl, methylthiomethyl, 1-methylthioethyl or 1-ethylthioethyl, or 2-oxa- or 2-thia-cycloalkyl having 5 or 6 ring atoms, for example 2-tetrahydrofuryl or 2-tetrahydropyranyl or corresponding thia analogues, and also unsubstituted or substituted 1-phenyl-lower alkyl, such as unsubstituted or substituted benzyl or diphenylmethyl, there being suitable as substituents of phenyl radicals, for example, halogen, such as chlorine, lower alkoxy, such as methoxy, and/or nitro. Further hydroxy-protecting groups are also organic silyl or stannyl radicals that preferably contain lower alkyl, especially methyl, and/or aryl, for example phenyl, as substituents, especially tri-lower alkylsilyl, especially trimethylsilyl, and also dimethyl-tert.-butyl-silyl, or correspondingly substituted stannyl, for example tri-n-butylstannyl.

Carboxy groups are preferably protected in esterified form, such ester groupings being readily cleavable under mild conditions. Carboxy groups protected in this manner contain as esterifying groups especially lower alkyl groups that are branched at the 1-position or suitably substituted at the 1- or 2-position. Preferred carboxy groups in esterified form are, inter alia, tert.-lower alkoxycarbonyl, for example tert.-butoxycarbonyl, α-aryl-lower alkoxycarbonyl having one or two aryl radicals, these being phenyl radicals that are unsubstituted or substituted, for example, by lower alkyl, such as tert.-lower alkyl, for example tert.-butyl, lower alkoxy, such as methoxy, hydroxy, halogen, for example chlorine, nitro and/or by phenyl, such as benzyloxycarbonyl that is unsubstituted or substituted, for example, as mentioned above, for example 4-methoxybenzyloxycarbonyl or 4-nitrobenzyloxycarbonyl, biphenylyl-lower alkoxycarbonyl in which biphenylyl substitutes the α-position, for example 2-(p-biphenylyl)-2-propoxycarbonyl, or diphenylmethoxycarbonyl that is unsubstituted or substituted, for example, as mentioned above, for example diphenylmethoxycarbonyl or di-(4-methoxyphenyl)-methoxycarbonyl, 1-lower alkoxy-lower alkoxycarbonyl, such as methoxymethoxycarbonyl, 1-methoxyethoxycarbonyl or 1-ethoxymethoxycarbonyl, 2,2-diaryl-ethoxycarbonyl in which aryl is phenyl that is unsubstituted or substituted, for example, by nitro, such as 4-nitrophenyl, such as 2,2-di-(4-nitrophenyl)-ethoxycarbonyl, wherein the two aryl, for example phenyl, radicals may also be bonded to one another, for example 2-(9-fluorenyl)-ethoxycarbonyl, 1-lower alkylthio-lower alkoxycarbonyl, such as 1-methylthiomethoxycarbonyl or 1-ethylthioethoxycarbonyl, aroylmethoxycarbonyl in which the aroyl group is benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(trisubstituted silyl)-ethoxycarbonyl in which each of the substituents, independently of the others, represents an aliphatic, araliphatic, cycloaliphatic or aromatic hydrocarbon radical that is unsubstituted or substituted, for example, by lower alkyl, lower alkoxy, aryl, halogen and/or by nitro, such as unsubstituted or correspondingly substituted lower alkyl, phenyl-lower alkyl, cycloalkyl or phenyl, for example 2-tri-lower alkylsilylethoxycarbonyl, such as 2-trimethylsilylethoxycarbonyl or 2-(methyl-di-(n-butyl)-silyl)-ethoxycarbonyl, or 2-triarylsilylethoxycarbonyl, such as 2-triphenylsilylethoxycarbonyl.

Preferred protected carboxy groups are, for example, tert.-lower alkoxycarbonyl, such as tert.-butoxycarbonyl, and benzyloxycarbonyl that is unsubstituted or substituted, for example, as mentioned above, such as 4-methoxy- or 4-nitrobenzyloxycarbonyl, or diphenylmethoxycarbonyl, and also 2-(trimethylsilyl)-ethoxycarbonyl.

A protected amino group can be, for example, in the form of a readily cleavable acylamino, arylmethylamino, etherified mercaptoamino, 2-acyl-lower alk-1-enylamino, silylamino or stannylamino group or in the form of an azido group.

In a corresponding acylamino group, acyl is, for example, the corresponding radical of an organic carboxylic acid having, for example, up to 18 carbon atoms, especially an alkanecarboxylic acid that is unsubstituted or substituted, for example, by halogen or aryl, or of benzoic acid that is unsubstituted or substituted, for example, by halogen, for example chlorine, lower alkoxy, for example methoxy, nitro, and/or by phenyl, or of a carbonic acid semi-ester. Such acyl groups are, for example, lower alkanoyl, such as formyl, acetyl or propionyl, halo-lower alkanoyl, such as 2-haloacetyl, especially 2-chloro-, 2-bromo- 2-iodo-, 2,2,2-trifluoro- or 2,2,2-trichloroacetyl, benzoyl that is unsubstituted or substituted, for example, by halogen, lower alkoxy, nitro and/or by phenyl, for example benzoyl, 4-chlorobenzoyl, 4-methoxybenzoyl or 4-nitrobenzoyl, or lower alkoxycarbonyl that is branched at the 1-position of the lower alkyl radical or suitably substituted at the 1-or 2-position, especially tert.-lower alkoxycarbonyl, for example tert.-butoxycarbonyl, α-aryl-lower alkoxycarbonyl having one or two aryl radicals that are preferably phenyl that is unsubstituted or substituted, for example, by lower alkyl, especially tert.-lower alkyl, such as tert.-butyl, lower alkoxy, such as methoxy, hydroxy, halogen, for example chlorine, nitro and/or by phenyl, such as unsubstituted or substituted benzyloxycarbonyl, for example 4-nitrobenzyloxycarbonyl, biphenylyl-lower alkoxycarbonyl in which biphenylyl substitutes the α-position, for example 2-(p-biphenylyl)-2-propoxycarbonyl), or substituted diphenylmethoxycarbonyl, for example benzhydryloxycarbonyl or di-(4-methoxyphenyl)-methoxycarbonyl, 2,2-diarylethoxycarbonyl in which aryl is phenyl that is unsubstituted or substituted, for example, by nitro, such as 4-nitrophenyl, such as 2,2-di-(4-nitrophenyl)-ethoxycarbonyl, wherein the two aryl, for example phenyl, radicals may also be bonded to one another, for example 2-(9-fluorenyl)-ethoxycarbonyl, aroylmethoxycarbonyl in which the aroyl group is preferably benzoyl that is unsubstituted or substituted, for example, by halogen, such as bromine, for example phenacyloxycarbonyl, 2-halo-lower alkalkoxycarbonyl, for example 2,2,2-trichloroethoxycarbonyl, 2-bromoethoxycarbonyl or 2-iodoethoxycarbonyl, or 2-(tri-substituted silyl)-ethoxycarbonyl in which each of the substituents, independently of the others, is an aliphatic, araliphatic, cycloaliphatic or aromatic hydrocarbon radical that has up to 15 carbon atoms and is unsubstituted or substituted, for example, by lower alkyl, lower alkoxy, aryl, halogen or by nitro, such as corresponding unsubstituted or substituted lower alkyl, phenyl-lower alkyl, cycloalkyl or phenyl, for example 2-tri-lower alkylsilylethoxycarbonyl, such as 2-trimethylsilylethoxycarbonyl or 2-(di-n-butyl-methyl-silyl)-ethoxycarbonyl, or 2-triarylsilylethoxycarbonyl, such as 2-triphenylsilylethoxycarbonyl.

Further acyl radicals suitable as amino-protecting groups are also corresponding radicals of organic phosphoric, phosphonic or phosphinic acids, such as di-lower alkylphosphoryl, for example dimethylphosphoryl, diethylphosphoryl, di-n-propylphosphoryl or diisopropylphosphoryl, dicycloalkylphosphoryl, for example dicyclohexylphosphoryl, unsubstituted or substituted diphenylphosphoryl, for example diphenylphosphoryl, di-(phenyl-lower alkyl)-phosphoryl that is unsubstituted or substituted, for example, by nitro, for example dibenzylphosphoryl or di-(4-nitrobenzyl)-phosphoryl, unsubstituted or substituted phenoxyphenylphosphonyl, for example phenoxyphenylphosphonyl, di-lower alkylphosphinyl, for example diethylphosphinyl, or unsubstituted or substituted diphenylphosphinyl, for example diphenylphosphinyl.

In an arylmethylamino group, which may be a mono-, di- or especially tri-arylmethylamino group, the aryl radicals are especially unsubstituted or substituted phenyl radicals. Such groups are, for example, benzylamino, diphenylmethylamino and especially tritylamino.

An etherified mercapto group in an amino group protected by such a radical is especially arylthio or aryl-lower alkylthio in which aryl is especially phenyl that is unsubstituted or substituted, for example, by lower alkyl, such as methyl or tert.-butyl, lower alkoxy, such as methoxy, halogen, such as chlorine, and/or by nitro. A corresponding amino-protecting group is, for example, 4-nitrophenylthio.

In a 2-acyl-lower alk-1-en-1-yl radical that may be used as an amino-protecting group, acyl is, for example, the corresponding radical of a lower alkanecarboxylic acid, of a benzoic acid that is unsubstituted or substituted, for example, by lower alkyl, such as methyl or tert.-butyl, lower alkoxy, such as methoxy, halogen, such as chlorine, and/or by nitro, or especially of a carbonic acid semi-ester, such as a carbonic acid lower alkyl semi-ester. Corresponding protecting groups are especially 1-lower alkanoylprop-1-en-2-yl, for example 1-acetylprop-1-en-2-yl, or 1-lower alkoxycarbonylprop-1-en-2-yl, for example 1-ethoxycarbonyl-prop-1-en-2-yl.

An amino group can also be protected in protonated form; as corresponding anions there come into consideration especially those of strong inorganic acids, such as hydrohalic acids, for example the chloride or bromide anion, or organic sulfonic acids, such as p-toluenesulfonic acid.

Preferred amino-protecting groups are acyl radicals of carbonic acid semi-esters, especially tert.-butoxycarbonyl, or benzyloxycarbonyl that is unsubstituted or substituted, for example as indicated, for example 4-nitrobenzyloxycarbonyl, or diphenylmethoxycarbonyl, 2-(9-fluorenyl)-ethoxycarbonyl, or 2-halo-lower alkoxycarbonyl, such as 2,2,2-trichloroethoxycarbonyl, and also trityl or formyl.

Unsubstituted carbamoyl groups are protected, for example, in the form of N-(9-xanthenyl) derivatives or in the form of N-(mono-, di- or tri-arylmethyl) derivatives, in which aryl is especially phenyl that is unsubstituted or contains up to 5 identical or different substituents, preferably lower alkyl, such as methyl, or lower alkoxy, such as methoxy. The following may be mentioned as examples of such arylmethyl protecting groups: 4-methoxybenzyl, 2,4,6-trimethoxybenzyl, diphenylmethyl, di-(4-methoxyphenyl)-methyl, di-(4-methylphenyl)-methyl and (4-methylphenyl)-([polymeric carrier]-phenyl)-methyl. A preferred carbamoyl-protecting group is trityl.

Guanidino groups may be protected, for example, by means of suitably substituted sulfonyl groups, such as arylsulfonyl in which aryl is phenyl that is unsubstituted or contains, for example, lower alkyl, such as methyl, or benzoheterocyclyl, such as chromanyl, that is unsubstituted or substituted, for example, by lower alkyl, such as methyl, and bonded by way of an aromatic carbon atom, such as 4-methoxyphenylsulfonyl or 2,2,5,7,8-pentamethyl-6-chromanylsulfonyl.

In this Application there is to understood by a protecting group, especially a carboxy-protecting group, also a polymeric carrier that is bonded to the functional group to be protected, especially to a carboxy group, which carrier is suitable especially for the so-called Merrifield peptide synthesis and can be readily removed. Such a polymeric carrier is, for example, preferably a polystyrene resin weakly crosslinked by copolymerisation with divinylbenzene, which resin carries bridging members suitable for the reversible bonding of amino acid and peptide residues. Especially in connection with the above-mentioned weakly crosslinked polystyrene resin, these bridging members are especially methylene groups that are unsubstituted or substituted and that are bonded directly to aromatic radicals of the polystyrene resin. Substituents of the methylene groups are bonded to the methylene groups preferably by ether or ester groupings and contain suitable functional groupings that together with functional groups, especially carboxy groups, of the amino acid or peptide fragment, can form protected groups, especially corresponding carboxy groups, such as esterified carboxy groups. Such bridging members are, for example, the divalent radicals of 4-methoxybenzyl alcohols optionally containing in the α-position phenyl that is unsubstituted or substituted, for example in the o- and/or p-position, for example by lower alkoxy, such as methoxy, in which 4-methoxybenzyl alcohols the carbon atom of the 4-methoxy group is bonded directly to a phenyl radical of the polystyrene resin, and the benzylic hydroxy group esterifies the carboxy function of the amino acid or of the peptide fragment.

The reaction to form the amide bond can be carried out in a manner known per se, the reaction conditions depending especially on whether and how the carboxy group that participates in the reaction has been activated, customarily in the presence of a suitable solvent or diluent or a mixture thereof, and, if necessary, in the presence of a condensing agent which, for example, if the carboxy group that participates in the reaction is present in the form of an anhydride, may also be a suitable acid-binding agent, with cooling or heating, for example in a temperature range of from approximately −30° C. to approximately +150° C., especially from +10° C. to +70° C., preferably from room temperature (approximately +20° C.) to +50° C., in a closed reaction vessel and/or in the atmosphere of an inert gas, for example nitrogen.

Customary condensing agents are, for example, carbodiimides, for example N,N'-diethyl-, N,N'-diisopropyl-, N,N'-dicyclohexyl- or N-ethyl-N'-(3-dimethylaminopropyl)-carbodiimide, suitable carbonyl compounds, for example carbonyldiimidazole, or 1,2-oxazolium compounds, for example 2-ethyl-5-phenyl-1,2-oxazolium-3'-sulfonate and 2-tert.-butyl-5-methylisoxazolium perchlorate, or a suitable acylamino compound, for example 2-ethoxy-1-ethoxycarbonyl-1,2-dihydroquinoline. Customary acid-binding condensing agents are, for example, alkali metal carbonates or bicarbonates, for example sodium or potassium carbonate or bicarbonate (customarily together with a sulfate), or organic bases, such as customarily sterically hindered tri-lower alkylamines, for example N,N-diisopropyl-N-ethylamine.

The above-mentioned Merrifield peptide synthesis is suitable especially for a semi-automatic or fully automatic synthesis of compounds with the amino acid sequence of formula I, wherein amino acids and/or peptide fragments in which functional groups not participating in the reaction are usually in protected form are linked to one another by way of amide groupings without isolation of the peptide fragments formed. One of the functional groups, normally the terminal carboxy group present in the end peptide, is optionally bonded to a suitable polymeric carrier by a bridging member, as described. In principle this process variant is carried out analogously to the customary synthesis of peptides, care being taken that, in the already synthesised peptide fragment that contains the polymeric carrier moiety, the freeing, from the protected group, of the functional group that participates in the reaction, usually the terminal amino group, is in each case carried out under conditions in which the protecting groups of the functional groups not participating in the reaction are retained.

The removal of carboxy-, amino-, hydroxy-, carboxylic acid amide-, carbamoyl- and/or guanidino-protecting groups is carried out in a manner known per se, for example by means of solvolysis, especially hydrolysis (under acid or basic conditions), alcoholysis, acidolysis or treatment with a base, or by means of reduction, especially hydrogenolysis or chemical reduction, optionally in stages or simultaneously, it also being possible to use enzymatic methods.

Thus, tert.-lower alkoxycarbonyl, or lower alkoxycarbonyl substituted in the 2-position by an organic silyl group or in the 1-position by lower alkoxy or lower alkylthio, or unsubstituted or substituted diphenylmethoxycarbonyl, can be converted into free carboxy by acidolysis, for example by treatment with a suitable acid, such as a lower alkanecarboxylic acid which may contain halogen, for example formic acid or trifluoroacetic acid, with or without the addition of a nucleophilic compound, such as phenol or anisole. Unsubstituted or substituted benzyloxycarbonyl can be freed, for example, by hydrogenolysis, that is to say by treatment with hydrogen in the presence of a metallic hydrogenation catalyst, such as a palladium catalyst. In addition, suitably substituted benzyloxycarbonyl, such as 4-nitrobenzyloxycarbonyl, can be converted into free carboxy also by chemical reduction, for example by treatment with an alkali metal dithionite, for example sodium dithionite, or with a reducing metal, for example zinc, or a reducing metal salt, such as a chromium-(II) salt, for example chromium(II) chloride, usually in the presence of a hydrogen donor that, together with the metal, is capable of producing nascent hydrogen, such as an acid, especially a suitable carboxylic acid, such as a lower alkanecarboxylic acid that is unsubstituted or substituted, for example, by hydroxy, for example acetic acid, formic acid, glycolic acid, diphenylglycolic acid, lactic acid, mandelic acid, 4-chloromandelic acid or tartaric acid, or an alcohol or thiol, water preferably being added. 2,2-Diarylethoxycarbonyl or 2-(9-fluorenyl)-ethoxycarbonyl groups can be cleaved under mild basic conditions, for example by treatment with piperidine. By treatment with a reducing metal or metal salt, as described above, it is also possible to convert 2-halo-lower alkoxycarbonyl (optionally after conversion of a 2-bromo-lower alkoxycarbonyl group into a corresponding 2-iodo-lower alkoxycarbonyl group) or aroylmethoxycarbonyl into free carboxy, it being possible to cleave aroylmethoxycarbonyl also by treatment with a nucleophilic, preferably salt-forming, reagent, such as sodium thiophenolate or sodium iodide. Substituted 2-silylethoxycarbonyl can also be converted into free carboxy by treatment with a salt of hydrofluoric acid yielding the fluoride anion, such as an alkali metal fluoride, for example sodium or potassium fluoride, in the presence of a macrocyclic polyether ("crown ether"), or with a fluoride or an organic quaternary base, such as tetra-lower alkylammonium fluoride or tri-lower alkylarylammonium fluoride, for example tetraethylammonium fluoride or tetrabutylammonium fluoride, in the presence of an aprotic polar solvent, such as dimethyl sulfoxide or N,N-dimethylacetamide.

A protected amino group is freed in a manner known per se and, depending on the nature of the protecting groups, by various methods, but preferably by solvolysis or reduction. 2-Halo-lower alkoxycarbonylamino (optionally after conversion of a 2-bromo-lower alkoxycarbonylamino group into a 2-iodo-lower alkoxycarbonylamino group), aroylmethoxycarbonylamino or 4-nitrobenzyloxycarbonylamino can be cleaved, for example, by treatment with a suitable chemical reducing agent, such as zinc in the presence of a suitable carboxylic acid, such as aqueous acetic acid. Aroylmethoxycarbonylamino can also be cleaved by treatment with a nucleophilic, preferably salt-forming, reagent, such as sodium thiophenolate, and 4-nitrobenzyloxycarbonylamino also by treatment with an alkali metal dithionite, for example sodium dithionite. Unsubstituted or substituted diphenylmethoxycarbonylamino, tert.-lower alkoxycarbonylamino or 2-trisubstituted silylethoxycarbonylamino can be cleaved by treatment with a suitable acid, such as a lower alkanecarboxylic acid that is unsubstituted or substituted, for example, by halogen, such as fluorine, for example formic acid or trifluoroacetic acid, and 2,2-diarylethoxycarbonylamino, such as 2,2-di-(4-nitrophenyl)-ethoxycarbonylamino, and also 2-(9-fluorenyl)-ethoxycarbonylamino, by treatment with a suitable base, such as an aliphatic, preferably secondary, amine, for example piperidine. The amino group can be freed from unsubstituted or substituted benzyloxycarbonylamino, for example, by hydrogenolysis, that is to say by treatment with hydrogen in the presence of a suitable hydrogenation catalyst, such as a palladium catalyst, from unsubstituted or substituted triarylmethylamino or formylamino, for example, by treatment with an acid, such as a mineral acid, for example hydrochloric acid, or an organic acid, for example formic, acetic or trifluoroacetic acid, in the presence or absence of water, and from an organic silylamino group, for example, by hydrolysis or alcoholysis. An amino group protected by 2-haloacetyl, for example 2-chloroacetyl, can be freed, for example, by treatment with thiourea in the presence of a base, or with a thiolate salt, such as an alkali metal thiolate, of thiourea, and by subsequent solvolysis, such as alcoholysis or hydrolysis, of the resulting condensation product. An amino group protected by 2-substituted silylethoxycarbonyl can also be converted into the free amino group by treatment with a salt of hydrofluoric acid yielding fluoride anions, as described above in connection with the freeing of a correspondingly protected carboxy group.

Amino protected in the form of an azido group can be converted into free amino, for example, by reduction, for example by catalytic hydrogenation with hydrogen in the presence of a hydrogenation catalyst, such as platinum oxide, palladium or Raney nickel, or alternatively by treatment with zinc in the presence of an acid, such as acetic acid. The catalytic hydrogenation can preferably be carried out in an inert solvent, such as a halogenated hydrocarbon, for example methylene chloride, or alternatively in water or a mixture of water and an organic solvent, such as an alcohol or dioxan, at approximately from 20° C. to 25° C., or alternatively with cooling or heating.

A hydroxy group protected by a suitable acyl group, an organic silyl group or by unsubstituted or substituted 1-phenyl-lower alkyl can be freed analogously to a correspondingly protected amino group. A hydroxy group protected by 2,2-dichloroacetyl can be freed, for example, by basic hydrolysis, and a hydroxy group etherified by tert.-lower alkyl, for example tert.-butyl, or by a 2-oxa- or 2-thia-aliphatic or -cycloaliphatic hydrocarbon radical can be freed by acidolysis, for example by treatment with a mineral acid or a strong carboxylic acid, for example trifluoroacetic acid.

A carboxylic acid amide group protected by 9-xanthenyl can be freed, for example, by treatment with hydrogen bromide in glacial acetic acid or with hydrogen fluoride in the presence of anisole. A carboxylic acid amide group protected by mono-, di- or tri-arylmethyl can be freed, for example, by treatment with hydrogen fluoride in the presence of anisole; furthermore, a diphenylmethyl protecting group can be removed, for example, by hydrogenolysis in the presence of a palladium-on-carbon catalyst, and a di-(4-methoxyphenyl)-methyl protecting group or a 2,4,6-trimethoxybenzyl protecting group can be removed, for example, by treatment with trifluoroacetic acid.

Guanidino groups protected by organic sulfonyl groups, such as 4-methylphenylsulfonylguanidino or 2,2,5,7,8-pentamethyl-6-chromanylsulfonylguanidino, can be freed, for example, by treatment with a suitable acid, such as trifluoroacetic acid.

A protected functional group, especially a corresponding carboxy group, in which the protecting group simultaneously acts as a carrier material in the mentioned Merrifield peptide synthesis, can be cleaved in a manner known per se, for example as described above. A correspondingly esterified carboxy group that is bonded to the polymeric carrier material by way of a suitable bridging member is cleaved in accordance with the nature of the bridging member. For example, a carboxy group bonded to the polymeric carrier material by way of an ester grouping having an activated benzylic bridging member, for example a 4-methoxybenzyloxycarbonyl group, in which the carbon atom of the methoxy group is bonded, for example, to a phenyl radical of the polystyrene resin weakly crosslinked with divinylbenzene, can be freed analogously to the above-mentioned unsubstituted or substituted benzyloxycarbonyl groups, for example by treatment with a suitable acid, such as trifluoroacetic acid.

If desired, if several protected functional groups are present, the protecting groups can be so selected that more than-one of these protecting groups can be removed at the same time, for example by acidolysis, such as by treatment with trifluoroacetic acid or formic acid, or by reduction, such as by treatment with zinc and acetic acid, or with hydrogen and a hydrogenation catalyst, such as a palladium-on-carbon catalyst.

Process b

The transformed host cells used for the manufacture of the polypeptides of the invention are produced as follows:

- a DNA coding for a polypeptide of the invention is produced,
- a hybrid vector containing that DNA is produced, and
- a suitable host strain is transformed with the said hybrid vector.

The DNA coding for a polypeptide of the invention is corresponding chromosomal DNA isolated from a human gene bank by known processes, cDNA isolated by the mRNA route, or corresponding synthetic DNA. The latter is produced according to generally known processes, for example in accordance with the method described by S. A. Narang [Tetrahedron 39, 3 (1983)] or the method described in European Patent Application No. 146785, especially using commercially obtainable DNA synthesis machines.

A corresponding DNA coding for PCATFP has the following sequence $Z_1$-$Y_{13}$-$Y_1$-$Y_{15}$-$Y_{14}$-$Y_2$-$Y_{16}$-$Y_1$-$Y_{11}$-$Y_7$-$Y_{16}$-$Y_{16}$-
$Y_{15}$-$Y_1$-$Y_4$-$Y_{15}$-$Y_1$-$Y_9$-$Y_{11}$-$Y_{16}$-$Y_7$-$Y_4$-$Y_7$-$Y_1$-
$Y_2$-$Y_{11}$-$Y_{11}$-$Y_{11}$-$Y_1$-$Y_1$-$Y_{11}$-$Y_3$-$Y_6$-$Y_4$-$Y_5$-$Y_3$-
$Y_6$-$Y_{13}$-$Y_{12}$-$Y_1$-$Y_{16}$-$Y_7$-$Y_{11}$-$Y_7$-$Y_6$-$Y_7$-$Y_6$-$Y_7$-
$Y_2$-$Y_7$-$Y_8$-$Y_{16}$-$Y_{16}$-$Y_{11}$-$Y_4$-$Y_{16}$-$Y_{15}$-$Y_2$-$Y_{16}$-$Y_{17}$-$Z_2$

- $Y_1$ codes for alanine (Ala) and is GCT, GCC, GCA or GCG,
- $Y_2$ codes for arginine (Arg) and is CGT, CGC, CGA, CGG, AGA or AGG,
- $Y_3$ codes for valine (Val) and is GTT, GTC, GTA or GTG,
- $Y_4$ codes for aspartic acid (Asp) and is GAT or GAC,
- $Y_5$ codes for tyrosine (Tyr) and is TAT or TAC,
- $Y_6$ codes for glutamine (Gln) and is CAA or CAG,
- $Y_7$ codes for glutamic acid (Glu) and is GAA or GAG,
- $Y_8$ codes for glycine (Gly) and is GGT, GGC, GGA or GGG,
- $Y_9$ codes for threonine (Thr) and is ACT, ACC, ACA or ACG,
- $Y_{10}$ codes for isoleucine (Ile) and is ATT, ATC or ATA,
- $Y_{11}$ codes for leucine (Leu) and is TTA, TTG, CTT, CTC, CTA or CTG
- $Y_{12}$ codes for lysine (Lys) and is AAA or AAG,
- $Y_{13}$ codes for methionine (Met) and is ATG,
- $Y_{14}$ codes for phenylalanine (Phe) and is TTT or TTC.
- $Y_{15}$ codes for proline (Pro) and is CCT, CCC, CCA or CCG,
- $Y_{16}$ codes for serine (Ser) and is TCT, TCC, TCA, TCG, AGT or AGC,
- $Y_{17}$ represents TAA, TAG or TGA (stop codon), and
- $Z_1$ and $Z_2$ are flanking DNA regions containing from 5 to 100, especially from 5 to 15, nucleotides that each contain a restriction enzyme recognition sequence.

The invention relates especially to DNAs coding for PCATFP and PCGRPATFP that contain triplets preferred by E. coli or S. cerevisiae.

A preferred DNA coding for PCATFP has the following sequence (with the restriction enzyme cleavage sites shown)

```
5'          Met Ala Pro Phe Arg Ser Ala Leu Glu Ser Ser Pro Ala Asp Pro Ala Thr        (III)
    CTGGAATTCATGGCTCCGTTCCGTTCTGCTCTGGAATCTTCTCCGGCTGACCCGGCTACC
    GACCTTAAGTACCGAGGCAAGGCAAGACGAGACCTTAGAAGAGGCCGACTGGGCCGATGG
3'      ------
         EcoRI

Leu Ser Glu Asp Glu Ala Arg Leu Leu Leu Ala Ala Leu Val Gln Asp Tyr Val Gln Met
    CTGTCTGAAGACGAAGCTCGTCTGCTGCTAGCTGCTCTGGTTCAGGACTACGTTCAGATG
    GACAGACTTCTGCTTCGAGCAGACGACGATCGACGAGACCAAGTCCTGATGCAAGTCTAC
                              ------
                               NheI

Lys Ala Ser Glu Leu Glu Gln Glu Gln Glu Arg Glu Gly Ser Ser Leu Asp Ser Pro Arg
    AAAGCTTCTGAACTGGAACAGGAACAGGAACGTGAAGGTTCTTCTCTGGACTCTCCGCGT
    TTTCGAAGACTTGACCTTGTCCTTGTCCTTGCACTTCCAAGAAGAGACCTGAGAGGCGCA

SerNON        3'
    TCTTAGGATCCTG
    AGAATCCTAGGAC
         ------5'
          BamHI
``` whilst a DNA coding for PCGRPATFP has the following sequence $Z_1$-$Y_{13}$-$Y_1$-$Y_{15}$-$Y_{14}$-$Y_2$-$Y_{16}$-$Y_1$-$Y_{11}$-$Y_7$-$Y_{16}$-$Y_{16}$-
$Y_{15}$-$Y_1$-$Y_4$-$Y_{15}$-$Y_1$-$Y_9$-$Y_{11}$-$Y_{16}$-$Y_7$-$Y_4$-$Y_7$-$Y_1$-
$Y_2$-$Y_{11}$-$Y_{11}$-$Y_{11}$-$Y_1$-$Y_1$-$Y_{11}$-$Y_3$-$Y_6$-$Y_4$-$Y_5$-$Y_3$-
$Y_6$-$Y_{13}$-$Y_{12}$-$Y_1$-$Y_{16}$-$Y_7$-$Y_{11}$-$Y_7$-$Y_6$-$Y_7$-$Y_6$-$Y_7$-
$Y_2$-$Y_7$-$Y_8$-$Y_{16}$-$Y_2$-$Y_{10}$-$Y_{10}$-$Y_1$-$Y_6$-$Y_{17}$-$Z_2$, wherein The oligonucleotide of formula III is prepared, for example, in accordance with the process described in European Patent Application No. 168342, by synthesising chemically the partial sequences underlined in formula III, kinasing, making up to duplexes using DNA polymerase and the four nucleoside triphosphates, and ligating by way of the inserted restriction cleavage sites to form the PCATFP gene.

The invention relates furthermore to expression vectors that contain a DNA sequence coding for PCATFP or PCGRPATFP and regulated by an expression control sequence.

The expression vectors of the present invention are prepared, for example, by inserting a DNA sequence coding for a polypeptide of the invention into a vector DNA that contains an expression control sequence in such a manner that the expression control sequence regulates the said DNA sequence.

The choice of a suitable vector is based on the host cell provided for the transformation. Suitable hosts are, for example, microorganisms, such as yeasts, for example Saccharomyces cerevisiae, and bacterial strains, especially strains of Escherichia coli, Bacillus subtilis, Bacillus stearothermophilus, Pseudomonas, Haemophilus, Streptococcus, and others, and also cells of higher organisms, especially established human or animal cell lines.

There are suitable, in principle, all those vectors that are capable of replicating and expressing in the selected host the heterologous DNA sequences that code for the polypeptides of the invention.

Examples of vectors that are suitable for the expression of a gene in a strain of E. coli are bacteriophages, for example derivatives of the bacteriophage λ, or plasmids, such as, especially, the plasmid colE1 and its derivatives, for example pBR322. Suitable vectors contain an intact replicon and a marker gene that renders possible the selection and identification of the microorganisms transformed by the expression plasmids by means of a phenotypic trait. Suitable marker genes impart to the microorganism, for example, resistance to heavy metals, antibiotics and the like. Furthermore, preferred vectors contain, outside the replicon and marker gene regions, recognition sequences for restriction endonucleases, so that the DNA sequence coding for the polypeptide of the invention and optionally the expression control sequences can be inserted at these sites. Plasmid pBR322 contains an intact replicon and marker genes ($tet^R$ and $amp^R$) imparting resistance to tetracycline and ampicillin.

Several expression control sequences can be used for regulating the polypeptide expression. There are used especially expression control sequences of strongly expressed genes of the host cell to be transformed. When using pBR322 as hybrid vector and E. coli as host microorganism, suitable expression control sequences (which, inter alia, contain the promotor and the ribosomal binding site) are, for example, those of the lactose operon, the tryptophan operon, the arabinose operon and the like, and of the β-lactamase gene, the corresponding sequences of the phage λN-gene or of the phage fd-layer protein gene, and others. Whereas the promotor of the β-lactamase gene (β-lac-gene) is already contained in plasmid pBR322, the other expression control sequences must be inserted into the plasmid.

Vectors suitable for replication and expression in yeast contain a yeast-replication origin and a selective genetic marker for yeast. Hybrid vectors that contain a yeast replication origin, for example the chromosomal autonomously replicating segment (ars), are retained extrachromosomally within the yeast cell after transformation and are replicated autonomously during mitosis. Also, hybrid vectors that contain sequences homologous to the yeast 2µ plasmid DNA can be used. Such hybrid vectors are integrated by recombination of 2µ plasmids already present within the cell, or replicate autonomously. 2µ sequences are especially suitable for plasmids having a high transformation frequency and permit a high copy number. Suitable marker genes for yeast are especially those that impart antibiotic resistance to the host or, in the case of auxotrophic yeast mutants, genes that complement the host deficiency. Corresponding genes impart, for example, resistance to the antibiotic cycloheximide or provide for prototrophy in an auxotrophic yeast mutant, for example the URA3, LEU2, HIS3 or, especially, the TRP1 gene. Preferably, yeast hybrid vectors furthermore contain a replication origin and a marker gene for a bacterial host, especially E. coli, so that the construction and the cloning of the hybrid vectors and their precursors can be carried out in one bacterial host. Expression control sequences suitable for expression in yeast are, for example, those of the TRP1, ADHI or PHO5 gene, and also promotors involved in glycolytic degradation, for example the PGK and the GAPDH promotor.

The invention relates especially to expression vectors capable of replication and phenotypic selection that contain an expression control sequence and a DNA sequence coding for one of the polypeptides of the invention, wherein the said DNA sequence together with transcription start signal and termination signal and translation start signal and stop signal in the said expression plasmid is so arranged, with regulation of the said expression control sequence, that the polypeptides of the invention are expressed in a host cell transformed with the said expression plasmid.

In order to achieve effective expression, the gene must be correctly arranged ("in phase") with the expression control sequence. It is advantageous to link the expression control sequence in the region between the main mRNA origin and the ATG of a gene coding sequence that is linked naturally to the expression control sequence (for example the β-lac coding sequence when using the β-lac promotor), with the gene, which preferably brings with it its own translation start signal (ATG) and translation stop signal (for example TAG). An effective transcription and translation is thus ensured.

For example, a vector, especially pBR322, is cleaved with a restriction endonuclease and, optionally after modification of the resulting linearised vector, an expression control sequence provided with corresponding restriction ends is inserted. The expression control sequence contains at the 3'-end (in the translation direction) the recognition sequence of a restriction endonuclease, so that the vector already containing the expression control sequence can be digested with the said restriction enzyme, and the gene coding for one of the polypeptides of the invention and provided with matching ends can be inserted. The result is a mixture of two hybrid plasmids, which contain the gene in the correct and in the incorrect orientation, respectively. It is advantageous to cleave the vector already containing the expression control sequence with a second restriction endonuclease within the vector DNA and to insert into the resulting vector fragment the gene coding for one of the polypeptides of the invention provided with correct ends. All operations on the vector are carried out preferably in such a manner that the function of the replicon and of at least one marker gene is not impaired.

The vector construct may also contain a signal sequence that is operably joined to the expression control sequence and has the correct reading frame with respect to the gene coding for the polypeptide of the invention.

Suitable signal sequences are, for example, the OmpA, lpp, and β-lac signal sequences when using *E. coli* as host microorganism, and the invertase, α-factor and PHO5 signal sequences when using *S. cerevisiae* as host microorganism.

The transformation of the host cells with the expression plasmids of the invention is carried out according to known processes. The isolation of the transformed host cells is effected advantageously from a selective nutrient medium to which there has been added the biocide against which the marker gene contained in the expression plasmid imparts resistance. If, as preferred, the expression plasmids contain the $amp^R$ gene, ampicillin is accordingly added to the nutrient medium. Cells that do not contain the expression plasmid are destroyed in such a medium.

The invention relates also to the transformed host cells obtainable in the manner mentioned.

The culturing of the transformed host cells of the invention in accordance with process b) is effected in a manner known per se. For example, various carbon sources can be used for culturing the transformed host microorganisms of the invention. Examples of preferred carbon sources are assimilable carbohydrates, such as glucose, maltose, mannitol or lactose, or an acetate, which can be used either alone or in suitable mixtures. Suitable nitrogen sources are, for example, amino acids, such as casamino acids, peptides and proteins and their degradation products, such as tryprone, peptone or meat extracts; also yeast extracts, malt extract, and also ammonium salts, for example ammonium chloride, sulfate or nitrate, which can be used either alone or in suitable mixtures. Inorganic salts, which can also be used, are, for example, sulfates, chlorides, phosphates and carbonates of sodium, potassium, magnesium and calcium.

Furthermore, the medium contains, for example, growth-promoting substances, such as trace elements, for example iron, zinc, manganese and the like, and preferably substances that exert a selection pressure and prevent the growth of cells that have lost the expression plasmid. Thus, for example, ampicillin is added to the medium when the expression plasmid contains an $amp^R$ gene. Such an addition of antibiotically active substances also has the effect of destroying contaminating antibiotic-sensitive microorganisms.

Culturing is carried out in accordance with processes that are known per se. The culturing conditions, such as temperature, pH value of the medium and fermentation time, are so selected that maximum polypeptide titres are obtained. Thus, an *E. coli* or a yeast strain is preferably cultured under aerobic conditions in submersed culture with shaking or stirring at a temperature of approximately from 20° to 40° C., preferably approximately 30° C., and a pH value of from 4 to 8, preferably pH 7, for approximately from 4 to 20 hours, preferably from 8 to 12 hours.

When the cell density has reached an adequate value, culturing is terminated and the polypeptide of the invention is freed from the cells of the microorganism. For this purpose .the cells are destroyed, for example by treatment with a detergent, such as SDS or Triton, or are lysed with lysozyme or a similarly acting enzyme. Alternatively, or in addition, mechanical forces, such as shearing forces (for example X-press, French press, Dyno-mill) or shaking with glass beads or aluminium oxide, or alternate freezing, for example in liquid nitrogen, and thawing, for example to from 30° to 40° C., and ultrasound, can be used to break the cells. The resulting mixture, which contains proteins, nucleic acids and other cell constituents is, after centrifuging, enriched in a manner known per se with regard to the protein content. Thus, for example, the non-protein constituents are for the most part removed by polyethyleneimine treatment and the proteins, including the polypeptides of the invention, are precipitated, for example, by saturating the solution with ammonium sulfate or with other salts. Bacterial proteins can also be precipitated by means of acidification with acetic acid (for example 0.1%, pH 4–5). Other purification steps include, for example, chromatographic processes, such as ion exchange chromatography, gel permeation chromatography, partition chromatography, HPLC, reverse phase HPLC and the like. For example, separation of the constituents of the mixture is effected by dialysis, according to charge by means of gel electrophoresis or carrier-free electrophoresis, according to molecular size by means of a suitable Sephadex column, by affinity chromatography, for example with antibodies, especially monoclonal antibodies, or with thrombin coupled to a carrier suitable for affinity chromatography, or by other known processes.

For example, the isolation of an expressed polypeptide of the invention may comprise the following steps:

Separation of the cells from the culture solution by centrifugation; production of a crude extract by destroying the cells, for example by treatment with a lysing enzyme and/or alternate freezing/thawing; removal of insoluble constituents by centrifugation; precipitation of DNA by the addition of polyethyleneimine; precipitation of proteins by ammonium sulfate; ion exchange chromatography and/or reversed phase HPLC; removal of salts from the resulting solution by means of dialysis or chromatography on a suitable ion exchanger, for example Sephadex G25 or Sephadex G10.

Testing with suitable antibodies, for example monoclonal antibodies obtainable from hybridoma cells, can be used to detect the polypeptides of the invention.

There are usually obtained according to process b) peptides of formula I in which R is hydrogen, especially when expressing in yeast. In certain host cells, for example *E. coli*, an N-terminal acetylation can, however, occur, with the result that peptides of formula I in which R is acetyl are obtained.

In peptides of formula I obtainable according to the invention having a methionine radical containing a sulfoxide group, such a group is converted into the thio group in a manner known per se by reduction. For this suitable reducing agents, preferably iodide salts, such as ammonium iodide, are used, usually in the presence of a diluent, and resulting iodine can be removed, for example, by treatment with ascorbic acid.

Salts of compounds of formula I can be manufactured in a manner known per se. For example, salts of compounds of formula I that contain more acidic than basic groups can be formed, for example, by treatment with metal compounds, such as alkali metal salts of suitable organic carboxylic acids, for example the sodium salt of ?-ethylcaproic acid, or with inorganic alkali metal or alkaline earth metal salts, for example sodium bicarbonate, or with ammonia or a suitable organic amine, there preferably being used stoichiometric amounts or only a small excess of the salt-forming agent. Acid addition salts of compounds of formula I are obtained in customary manner, for example by treatment with an acid or a suitable anion exchange reagent. Internal salts of compounds of formula I that contain a free acidic group and a free basic group, can be formed, for example, by neutralising salts, such as acid addition salts, to the isoelectric point, for example with weak bases, or by treatment with liquid ion exchangers.

Salts can be converted in customary manner into the free compounds; metal and ammonium salts can be converted into the free compounds, for example, by treatment with suitable acids, and acid addition salts, for example, by treatment with a suitable basic agent.

The peptides of formula I have valuable pharmacological properties and can be used accordingly. If, for example, calvarian cells of chicken embryos or newborn rats are treated in vitro with peptides of formula I, stimulation of cell multiplication can be ascertained by way of the increase in the incorporation of tritium-labelled thymidine into the DNA. This stimulation can be achieved with concentrations of from approximately 1 to approximately 1000 nmol/l, and is most pronounced with concentrations of approximately 100 nmol/l, it being possible to ascertain the effect in the presence or absence of serum in the culture medium. The stimulating action of the peptides of formula I is specific to osteoblasts; for example skin fibroblasts of rats do not react. Unlike calcitonin or calcitonin gene related peptide, the peptides of formula I do not prevent bone resorption, which can be demonstrated in vitro in the calvarian system of mice.

Owing to these pharmacological activities, the peptides of formula I can be used, for example, for the treatment of diseases involving bone degeneration (osteopenia), such as osteoporosis, osteoarthritis, osteoarthrosis or Sudeck's disease, doses of from approximately 0.1 to approximately 10 mg/day being administered to a warm-blooded animal with a body weight of approximately 70 kg.

The invention thus relates also to a method of treating diseases involving bone degeneration in warm-blooded animals, which comprises administering to a warm-blooded animal having such a disease an effective dose of a peptide of formula I or a pharmaceutically acceptable salt thereof. Furthermore, the peptides of formula I can be used for the manufacture of diagnostic antibodies for detecting medullary thyroid carcinomas.

The invention relates also to pharmaceutical preparations that contain, as active ingredient, an effective dose, especially a dose effective for the treatment of the above-mentioned diseases, of one of the compounds of the invention or a salt thereof, preferably together with a carrier the proportion of which is usually more than 50% by weight. These are especially preparations that are suitable for intranasal or parenteral, such as subcutaneous, intramuscular or intravenous, administration to warm-blooded animals, such as humans, the dosage of the active ingredient depending on the species, the body weight, age and individual condition, the disease to be treated and the mode of administration.

The novel pharmaceutical preparations for parenteral administration contain, in a form ready for use, from approximately 0.01 to approximately 10% by weight, preferably from approximately 0.05 to approximately 1% by weight, of active ingredient. The pharmaceutical preparations according to the invention may be, for example, in unit dosage form, such as in ampoule form.

Preferably, solutions of the active ingredient, and also suspensions, especially isotonic aqueous solutions or suspensions, are used, and these, for example in the case of lyophilised preparations that contain the active ingredient on its own or together with a carrier, for example mannitol, can be prepared before use. For intranasal administration, suspensions in oil are especially suitable. The pharmaceutical preparations may be sterilised and may contain adjuncts, for example preservatives, stabilisers, wetting agents and/or emulsifiers, solubilisers, salts for regulating the osmotic pressure and/or buffers, and also viscosity-increasing substances, such as sodium carboxymethylcellulose, carboxymethylcellulose, dextran, polyvinylpyrrolidone or gelatine. They can be manufactured in a manner known per se, for example by means of conventional dissolving or lyophilising processes.

Suspensions in oil may contain, as oily component, the vegetable, synthetic or semi-synthetic oils customarily used for injection purposes. As such there may be mentioned especially liquid fatty acid esters that contain as acid component a long-chain fatty acid having from about 8 to about 22 carbon atoms, such as, for example, lauric acid, tridecylic acid, myristic acid, pentadecylic acid, palmitic acid, margaric acid, stearic acid, arachidic acid, behenic acid or corresponding unsaturated acids, such as, for example, oleic acid, elaidic acid, erucic acid, brassidic acid or linoleic acid. The alcohol component usually contains up to and including 7 carbon atoms and is a mono- or poly-hydric alcohol, for example methanol, ethanol, propanol, butanol or pentanol or isomers thereof, but especially glycol or glycerol. There may therefore be mentioned by way of example as fatty acid esters: ethyl oleate, isopropyl myristate, isopropyl palmitate, polyoxyethyleneglycerol trioleate (for example "Labrafil M 2735", manufactured by Gattefossé, Paris), triglycerides of saturated fatty acids having a chain length of from $C_8$ to $C_{12}$, (for example "Miglyol 812", manufactured by Chemische Werke, Witten/Ruhr, Germany) and also vegetable oils, such as cotton seed oil, almond oil, olive oil, castor oil, sesame oil, soybean oil or ground-nut oil.

The manufacture of the injection preparations is effected in customary manner under antimicrobial conditions, as is also the introduction thereof into ampoules or vials and the sealing of the containers.

The invention relates also to the use of compounds of formula I as pharmacological active ingredients or for the manufacture of pharmaceutical preparations, especially for the treatment of diseases involving bone degeneration, daily doses of from approximately 0.1 to approximately 10 mg preferably being administered.

Organic radicals and compounds referred to hereinbefore as "lower" contain up to and including 7, preferably up to and including 4, carbon atoms.

The following Examples illustrate the invention. Temperatures are in degrees Celsius.

EXAMPLE 1

1.1 The Fmoc-peptide/resin starting material obtainable in accordance with the process described below is subjected in a fully automatic peptide synthesis apparatus to the following reaction and washing operations, approximately 30 ml of washing liquid being used each time and the reaction vessel being shaken regularly; the reaction steps, unless stated otherwise, are carried out at room temperature:

single wash of the Fmoc-peptide/resin starting material with isopropanol for 0.8 minutes;
three washes, each of 0.4 minute's duration, with dimethylacetamide degassed under reduced pressure (dimethylamine-free);

eight treatments, each of 1.8 minutes' duration, with a 20% solution of piperidine in dimethylacetamide (removal of the Fmoc protecting group);

two washes, each of 0.4 minute's duration, with dimethylacetamide degassed under reduced pressure (dimethylamine-free);

single wash for 0.8 minutes with isopropanol;

three washes, each of 0.4 minute's duration, with dimethylacetamide degassed under reduced pressure (dimethylamine-free);

three washes, each of 0.4 minute's duration, with distilled 1-methyl-2-piperidone;

addition of the first coupling reagent, which has been prepared in the meantime as follows: 2.7 mmol of Fmoc-L-alanine are dissolved in 6.75 ml of a 0.4 molar mixture of 1-hydroxy-1H-benzotriazole in 1-methyl-2-piperidone, and 6.48 ml of a 0.5 molar solution of diisopropylcarbodiimide in 1-methyl-2-piperidone are added. The reaction mixture is maintained at room temperature for approximately 40 minutes and then used in that form. The coupling reaction itself takes 40 minutes, and the reaction mixture is maintained at 50°;

three washes, each of 0.4 minute's duration, with distilled 1-methyl-2-piperidone;

addition of the second coupling reagent, which has been prepared in the meantime and is of the same composition as the first and prepared in the same manner; the coupling reaction is carried out at 50° and takes 30 minutes (an almost complete reaction can be achieved with the second coupling reaction);

single wash for 0.4 minutes with dimethylacetamide degassed under reduced pressure (dimethylamine-free);

single treatment for 4.5 minutes with approximately 30 ml of a 1:1:8 mixture (v/v/v) of acetic anhydride, pyridine and dimethylacetamide (for the acetylation of amino groups that are still free, the N-acetylated compounds being removed in the subsequent working up process);

three washes, each of 0.4 minute's duration, with dimethylacetamide degassed under reduced pressure (dimethylamine-free);

single wash for 0.8 minutes with isopropanol;

three washes, each of 0.4 minute's duration, with dimethylacetamide degassed under reduced pressure (dimethylamine-free);

eight treatments, each of 1.8 minutes' duration, with a 20% solution of piperidine in dimethylacetamide (removal of the Fmoc protecting group);

two washes, each of 0.4 minute's duration, with dimethylacetamide degassed under reduced pressure (dimethylamine-free);

single wash for 0.8 minutes with isopropanol;

three washes, each of 0.4 minute's duration, with dimethylacetamide degassed under reduced pressure (dimethylamine-free); and three washes, each of 0.4 minute's duration, with distilled 1-methyl-2-piperidone.

After carrying out these process steps, the resulting peptide/resin compound is washed five times with isopropanol and dried under reduced pressure (high vacuum).

1.2. In order to remove the polymeric carrier, and if desired some of the acid-labile protecting groups, 1.1 g of the peptide/resin compound (approximately 0.1 mmol) obtainable in accordance with the above process are shaken for 5 minutes at room temperature in 6 ml of a 98:2 mixture (v/v) of trifluoroacetic acid (95%) and ethanedithiol, then filtered, and the filtration residue is treated again, for a period of 5 minutes, with the same amount of the trifluoroacetic acid/ethanedithiol mixture, then filtered. The filtration residue is then washed twice with 6 ml of 1,2-dichloroethane each time, and twice with 6 ml of trifluoroethanol each time. The combined filtrates and washing liquids are concentrated at room temperature under reduced pressure to a volume of approximately 5 ml, and the crude peptide is precipitated by the addition of 25 ml of a 1:1 mixture (v/v) of diisopropyl ether and petroleum ether (low-boiling). The precipitate is isolated by filtration and dried under reduced pressure (high pressure).

The protecting groups can be removed completely by dissolving the crude peptide in 5 ml of a 98:2 mixture (v/v) of trifluoroacetic acid (95%) and ethanedithiol; the solution is maintained at room temperature for 60 minutes, and the peptide is precipitated again by the addition of 25 ml of the 1:1 mixture (v/v) of diisopropyl ether and petroleum ether (low-boiling); this treatment is repeated again, the reaction time amounting to 50 minutes. The precipitate is dissolved in 20 ml of 10% aqueous acetic acid and lyophilised; the crude peptide is obtained in the form of a white powder.

1.3. For the reduction of any methionine sulfoxide which may be present, 0.1 g of the resulting crude peptide is dissolved in 1 ml of trifluoroacetic acid (90%), a solution of 0.015 g of ammonium iodide in 0.1 ml of water is added, and after 10 minutes the peptide is precipitated at room temperature by the addition of 6 ml of a 1:1 mixture (v/v) of diisopropyl ether and petroleum ether (low-boiling). The reddish oil so obtained is dissolved in 2 ml of 10% aqueous acetic acid, and a total of 0.01 g of ascorbic acid is added in portions until the solution is completely colourless. The solution is subjected to gel filtration, for which a column of a polyacrylamide product with a separating range of from 1000 to 6000 (Biogel-P6 column, manufactured by Bio-Rad) is used. Elution is carried out with 10% aqueous acetic acid, and the desired crude peptide is obtained as the first fraction after washing out with approximately 40 ml; the product is obtained in the form of a white powder by lyophilisation.

265 mg of Biogel-filtered product are partitioned in a countercurrent partitioning apparatus with 3 ml phase volume in the system tert.-amyl alcohol/acetic acid/water (4:2:5; v:v:v) over 1900 stages starting at vessels 3–5. 2 boundary fractions are taken from vessels 33–39 and vessels 81–90. The material obtained after concentration in vacuo and lyophilisation of the highly purified main fraction from vessels 40–80 is further processed.

1.4. For purification, 0.065 g of the crude peptide so obtainable is dissolved in 6.5 ml of 20% aqueous acetic acid and subjected in two portions (2.2 ml and 4.3 ml) to high pressure liquid chromatography under the following conditions: the column, measuring 20×250 mm, consists of silica gel, charged with aliphatic chains (Nucleosil 7C18, manufactured by Macherey-Nagel, Düren, Federal Republic of Germany) and 0.1% aqueous trifluoroacetic acid is used as eluant (A) and a 0.1% solution of trifluoroacetic acid in acetonitrile is used as eluant (B). The linear gradient is 15% B→45% B in 50 minutes, 45% B→60% B in 10 minutes, 60% B→100% B in 10 minutes, the throughput speed 18 ml/min and the detection in UV light 215 nm. The main fraction, with a retention time of approximately 45 minutes, is collected, concentrated under reduced pressure (high vacuum) and then lyophilised. In this manner the peptide PCATFP of formula CH₃—CO—Ala—Pro—Phe—Arg—Ser—Ala—Leu—Glu—Ser—Ser—
Pro—Ala—Asp—Pro—Ala—Thr—Leu—Ser—Glu—Asp—
Glu—Ala—Arg—Leu—Leu—Leu—Ala—Ala—Leu—Val—
Gln—Asp—Tyr—Val—Gln—Met—Lys—Ala—Ser—Glu—
Leu—Glu—Gln—Glu—Gln—Glu—Arg—Glu—Gly—Ser—
Arg—Ile—Ile—Ala—Gln—OH.

is obtained in the form of a white powder.

The high pressure liquid chromatography (column: silica gel, charged with aliphatic chains (Nucleosil 5C18, manufactured by Macherey-Nagel Düren, Federal Republic of Germany); dimension: 4.6×250 mm, eluant A: 0.1% aqueous trifluoroacetic acid, and eluant B: 0.1% solution of trifluoroacetic acid in acetonitrile; linear gradient 0% B 90% B in 60 minutes; throughput speed: 1 ml/min; detection in UV light: 215 nm) for the homogeneous product so obtainable gives a retention time of 37.8 minutes. Plasma desorption mass spectrometry (257 Cf) gives the corresponding molecular weight.

FAB-MS: MH+ 6220 (calculated molecular weight: 6220), isoelectric point: 4.2 (calculated: 4.04).

The starting material can be obtained in the following manner: The construction of the peptide molecule is carried out according to the Merrifield synthesis starting from the so-called Fmoc-Ser(But)-p-benzyloxybenzyl ester-polystyrene resin (1% crosslinked) manufactured by Novabiochem, Läufelfingen, Switzerland), in which the carboxy group of L-serine, of which the amino group is protected by 9-fluorenyl-methoxycarbonyl (Fmoc) and the hydroxy group is protected by tert.-butyl (But), is esterified with 4-methoxybenzyl alcohol in which the carbon atom of the methoxy group is bonded to an aromatic ring of the polystyrene resin, 1% crosslinked with divinylbenzene, which simultaneously acts as a carrier. For this there is used a fully automatic peptide synthesis apparatus that is suitable for the alternate removal of the amino-protecting groups, in the present case the Fmoc group, and coupling of the Fmoc-amino acid derivatives without isolation of the peptide/resin intermediates obtainable at each step. In a first step, Fmoc-Arg(Pmc)-OH (Pmc: 2,2,5,7,8-pentamethyl-chroman-6-sulfonyl) is coupled with the Ser(But)/resin starting material, and then the other Fmoc amino acids are coupled in steps, in the following sequence, to the peptide/resin intermediate obtainable after each step: Fmoc-Pro-OH, Fmoc-Ser(But)-OH, Fmoc-Asp(OBut)-OH (the second carboxy group not participating in the reaction is in the form of the tert.-butyl ester), Fmoc-Leu, Fmoc-Ser(But)-OH, Fmoc-Ser(But)-OH, Fmoc-Gly-OH, Fmoc-Glu(OBut)-OH, Fmoc-Arg(Pmc)-OH, Fmoc-Glu(OBut)-OH, Fmoc-Gln-OH, Fmoc-Glu(OBut)-OH, Fmoc-Gln-OH, Fmoc-Glu(OBut)-OH, Fmoc-Leu-OH, Fmoc-Glu(OBut)-OH, Fmoc-Ser(But)-OH, Fmoc-Ala-OH, Fmoc-Lys(Boc)-OH, Fmoc-Met-OH, Fmoc-Gln-OH, Fmoc-Val-OH, Fmoc-Tyr(But)-OH, Fmoc-Asp(OBut)-OH, Fmoc-Gln-OH, Fmoc-Val-OH, Fmoc-Leu-OH, Fmoc-Ala-OH, Fmoc-Ala-OH, Fmoc-Leu-OH, Fmoc-Leu-OH, Fmoc-Leu-OH, Fmoc-Arg(Pmc)-OH, Fmoc-Ala-OH, Fmoc-Glu(OBut)-OH, Fmoc-Asp(OBut)-OH, Fmoc-Glu(OBut)-OH, Fmoc-Ser(But)-OH, Fmoc-Leu-OH, Fmoc-Thr(But)-OH, Fmoc-Ala-OH, Fmoc-Pro-OH, Fmoc-Asp(OBut)-OH, Fmoc-Ala-OH, Fmoc-Pro-OH, Fmoc-Ser(But)-OH, Fmoc-Ser(But)-OH, Fmoc-Glu(OBut)-OH, Fmoc-Leu-OH, Fmoc-Leu-OH, Fmoc-Ala-OH, Fmoc-Ser(But)-OH, Fmoc-Arg(Pmc)-OH, Fmoc-Phe-OH and Fmoc-Pro-OH. The individual steps are carried out in accordance with the following scheme, approximately 30 ml of the washing liquids being used in each case, with the individual operations, unless stated otherwise, being carried out at room temperature, and the reaction mixture being shaken regularly.

Starting from 2 g of the above-described Fmoc-Ser(But)/resin starting material, the following process steps, repeated for each step, are carried out:

single wash for 0.8 minutes with isopropanol;

three washes, each of 0.4 minute's duration, with dimethylacetamide degassed under reduced pressure (dimethylamine-free);

eight treatments, each of 1.8 minutes' duration, with a 20% solution of piperidine in dimethylacetamide (removal of the Fmoc protecting group);

two washes, each of 0.4 minute's duration, with dimethylacetamide degassed under reduced pressure (dimethylamine-free);

single wash for 0.8 minutes with isopropanol;

three washes, each of 0.4 minute's duration, with dimethylacetamide degassed under reduced pressure (dimethylamine-free);

three washes, each of 0.4 minute's duration, with distilled 1-methyl-2-piperidone;

addition of the first coupling reagent, which has been prepared in the meantime as follows: 2.7 mmol of the respective Fmoc-L-amino acid are dissolved in 6.75 ml of a 0.4 molar mixture of 1-hydroxy-1H-benzotriazole in 1-methyl-2-piperidone, and 6.48 ml of a 0.5 molar solution of diisopropylcarbodiimide in 1-methyl-2-piperidone are added. The reaction mixture is maintained at room temperature, with stirring, for about 40 minutes, and then used in that form. The coupling reaction itself takes 40 minutes, during which the reaction mixture is maintained at 50°;

three washes, each of 0.4 minute's duration, with distilled 1-methyl-2-piperidone;

addition of the second coupling reagent, which has been prepared in the meantime and is of the same composition as the first and prepared in the same manner; the coupling reaction is carried out at 50° and takes 30 minutes (an almost complete reaction can be achieved with the second coupling reaction);

single wash for 0.4 minutes with dimethylacetamide degassed under reduced pressure (dimethylamine-free);

single treatment for 4.5 minutes with approximately 30 ml of a 1:1:8 mixture (v/v/v) of acetic anhydride, pyridine and dimethylacetamide (for the acetylation of amino groups that are still free in the growing peptide chain);

three washes, each of 0.4 minute's duration, with dimethylacetamide degassed under reduced pressure (dimethylamine-free);

single wash for 0.8 minutes with isopropanol; and three washes, each of 0.4 minute's duration, with dimethylacetamide degassed under reduced pressure (dimethylamine-free).

In this manner there is obtained the Fmoc-peptide/resin intermediate used as starting material in the above Example and which has the following formula:

Fmoc—Pro—Phe—Arg(Pmc)—Ser(But)—Ala—Leu—Glu(OBut)—Ser(But)—Ser(But)—Pro—

Ala—Asp(OBut)—Pro—Ala—Thr(But)—Leu—Ser(But)—Glu(OBut)—Asp(OBut)—

Glu(OBut)—Ala—Arg(Pmc)—Leu—Leu—Leu—Ala—Ala—Leu—Val—Gln—Asp(OBut)—

Tyr(But)—Val—Gln—Met—Lys(Boc)—Ala—Ser(But)—Glu(OBut)—Leu—Glu(OBut)—

Gln—Glu(OBut)—Gln—Glu(OBut)—Arg(Pmc)—Glu(OBut)—Gly—Ser(But)—Ser(But)—

Leu—Asp(OBut)—Ser(But)—Pro—Arg(Pmc)—Ser(But)—resin, wherein "resin" denotes the carboxy group-esterifying polystyrene (1% crosslinked with divinylbenzene)-methoxy-4-phenylmethoxy radical.

EXAMPLE 2

Sterile Dry Substance for Injection 0.1 mg of the PCATFP peptide (Example 1) is dissolved in 1 ml of an aqueous solution together with 20 mg of mannitol. The solution is sterile-filtered and introduced under aseptic conditions into a 2 ml ampoule, deep-frozen and lyophilised. Before use, the lyophilisate is dissolved in 1 ml of distilled water or 1 ml of physiological saline, and the solution is administered, for example, intramuscularly or intravenously.

EXAMPLE 3

In a manner analogous to that described in Example 1, but by acetylating with acetic anhydride in the manner described in Example 1 the free amino group of the terminal alanine obtained after removing the Fmoc protecting group, the following is obtained:

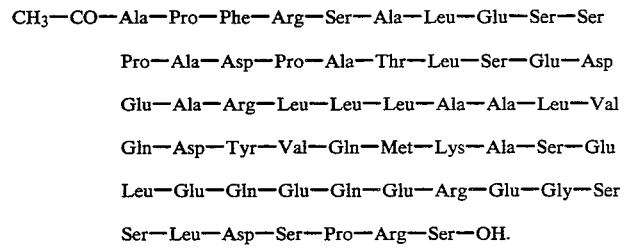

EXAMPLE 4

In a manner analogous to that described in Example 1, but starting from a synthetic resin prepared as described below, with linking of the protected amino acids corresponding to the structure of the desired end product but using Fmoc-Gln(trityl)-OH instead of Fmoc-Gln-OH, and with ultimate removal of all residual protecting groups with trifluoroacetic acid/water/1,2-ethanedithiol (95:5:5) for a period of 40 minutes at room temperature, the following is obtained

The starting materials are obtained as follows:

Fmoc-Gln(Trt)-OH

With vigorous stirring, 3.4 g of 9-fluorenylmethylsuccinimidinyl carbonate (10 mmol) are added to a solution of 4 g of the semihydrate of H-Gln(Trt)-OH (10 mmol) in 20 ml of tetrahydrofuran and 10 ml of 1N aqueous sodium hydroxide solution, and at the same time 1.4 ml of triethylamine is so added dropwise that the pH value is approximately 8.5. After 20 minutes the whole is cooled in an ice-bath, overlaid with ethyl acetate and acidified with 25 ml of 1M aqueous potassium hydrogen sulfate solution until a pH value of 2–2.5 is obtained. The organic phase is washed until neutral with water, dried over sodium sulfate and concentrated to 30 g under reduced pressure. The product is crystallised by the addition, in portions, of 35 ml of diisopropyl ether. After prolonged standing at reduced temperature, the crystalline material is isolated by filtration and washed once in a 1:4 mixture of ethyl acetate and diisopropyl ether and three times with diisopropyl ether. The Fmoc-Gln(Trt)-OH still contains 0.5 mol of diisopropyl ether even after prolonged drying under a high vacuum at 60°, m.p. from 125° (slow melting with the release of diisopropyl ether).

Fmoc-Gln(Trt)-OH

A mixture of 7.4 g of Fmoc-Gln-OH (20 mmol) and 10.4 g of triphenylmethanol (40 mmol) in 300 ml of acetic acid is stirred at 100° for 10 minutes. After the addition of 0.1 ml of concentrated sulfuric acid the whole is stirred at 100° for a further 15 minutes, a clear yellow solution forming. This is concentrated by evaporation under reduced pressure at 60°, and the residue is dried under reduced pressure for 10 minutes. The solid residue is dissolved in 60 ml of acetic acid at 60°, left at 60° for 20 minutes, then 2 ml of acetic anhydride (20 mmol) are added and after 1 hour at 60° the whole is concentrated by evaporation under reduced pressure. The oily residue is dried for 10 minutes at 60°, then dissolved in 100 ml of acetic acid and introduced dropwise into 500 ml of ice-cold water. The precipitate is isolated by filtration, washed well with water and dissolved in ethyl acetate; the aqueous phase is separated off and the organic phase is washed with a saturated aqueous sodium chloride solution. After drying over sodium sulfate, the organic solution is concentrated to dryness by evaporation, the residue is dissolved in 50 ml of 1,2-dichloroethane and applied to 100 g of silica gel; elution is carried out with 1,2-dichloroethane and with 1,2-dichloroethane containing 2%, then 4%, methanol. The fractions containing the Fmoc-Gln(Trt)-OH are concentrated by evaporation under reduced pressure, and the product is crystallised from a mixture of ethyl acetate and diisopropyl ether, m.p. from 125°.

Synthetic Resin 3.35 ml (23.4 mmol) of 2,6-dichlorobenzoyl chloride (Fluka) are added in 4 portions over a period of 5 hours to a suspension of 10 g of so-called 4-benzyloxybenzyl alcohol polystyrene (0.78 mmol OH/g; 1% crosslinked with divinylbenzene; the phenyl groups of the polystyrene are substituted in the 4-position by 4-hydroxymethylphenoxymethyl; Novabiochem), 15.6 mmol of Fmoc-Gln(Trt)-OH and 3.1 ml (38.5 mmol) of pyridine in 60 ml of dimethylacetamide, and the whole is stirred for 24 hours. The resin is isolated by filtration and thoroughly washed with methanol and 1,2-dichloroethane. The resin has a charge of 0.48 mmol/g (photometric Fmoc determination). The residual OH groups are acetylated for 2 hours with acetic anhydride/pyridine/dimethylacetamide 1:1:8 before the beginning of the peptide synthesis.

EXAMPLE 5

In a manner analogous to that described in Example 4, but by acetylation with acetic anhydride as described in Example 1 of the free amino group of the terminal alanine obtained after removal of the Fmoc protecting group, the following is obtained CH₃—CO—Ala—Pro—Phe—Arg—Ser—Ala—Leu—Glu—Ser—Ser—

Pro—Ala—Asp—Pro—Ala—Thr—Leu—Ser—Glu—Asp—

Glu—Ala—Arg—Leu—Leu—Leu—Ala—Ala—Leu—Val—

Gln—Asp—Tyr—Val—Gln—Met—Lys—Ala—Ser—Glu—

Leu—Glu—Gln—Glu—Gln—Glu—Arg—Glu—Gly—Ser—

Arg—Ile—Ile—Ala—Gln—OH.

What is claimed is:
1. A peptide of the formula

(I)

R—Ala—Pro—Phe—Arg—Ser—Ala—Leu—Glu—Ser—Ser—

Pro—Ala—Asp—Pro—Ala—Thr—Leu—Ser—Glu—Asp—

Glu—Ala—Arg—Leu—Leu—Leu—Ala—Ala—Leu—Val—

Gln—Asp—Tyr—Val—Gln—Met—Lys—Ala—Ser—Glu—

Leu—Glu—Gln—Glu—Gln—Glu—Arg—Glu—Gly—

—Ser—X—OH in which R is hydrogen or acetyl and X is an amino acid sequence of formula -Ser-Leu-Asp-Ser-Pro-Arg-Ser- (Ia) or of the formula -Arg-Ile-Ile-Ala-Gln- (Ib), in isolated, pure, or substantially pure form, or a salt of such a compound.

2. A peptide according to claim 1 of formula I, in which R is hydrogen and X has the meanings given in claim 1, or a pharmaceutically acceptable salt of such a compound.

3. A peptide of formula I according to claim 2, in which X is an amino acid sequence of formula -Ser-Leu-Asp-Ser-Pro-Arg-Ser- (Ia), or a pharmaceutically acceptable salt of such a compound.

4. A pharmaceutical preparation for the treatment of diseases involving bone degeneration containing an effective amount of a compound of formula I according to claim 1, or a pharmaceutically acceptable salt thereof, together with pharmaceutical carrier material.

5. A method of treating diseases involving bone degeneration in warm-blooded animals, which comprises administering to a warm-blooded animal with such a disease an effective dose of a peptide of formula I according to claim 1 or a pharmaceutically acceptable salt thereof.

6. A process for the manufacture of a peptide of formula I according to claim 1 or a salt of such a compound which comprises reacting an amide bond forming first fragment of a compound of formula I with a second amide bond forming fragment of a compound of formula I, said first fragment and said second fragment being complementary to one another such that an amide bond is formed between said first and second fragments to result in said compound of formula I, one of said first and second fragments containing a reactive free carboxy group or a reactive carboxylic acid derivative thereof and the other of said first and second fragments containing a free amino group or a reactive derivative thereof, wherein free carboxy, amino and hydroxy groups in said fragments, with the exception of the two groups participating in the reaction are in protected form and wherein free carbamoyl and guanidino groups can be in protected form, and protecting groups which may be present are removed, and in a compound so obtained having a sulfoxide group, converting said sulfoxide to a thio group, and, if desired, converting a salt so obtained to the corresponding free compound, or converting a free compound so obtained to a corresponding salt.

* * * * *